United States Patent
Barnett et al.

(10) Patent No.: US 6,412,488 B1
(45) Date of Patent: Jul. 2, 2002

(54) LOW CONTACT NASAL MASK AND SYSTEM USING SAME

(75) Inventors: Shari S. Barnett; Joseph M. Miceli, Jr., both of Pittsburgh, PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/310,548

(22) Filed: May 12, 1999

(51) Int. Cl.[7] .............................................. A62B 18/02
(52) U.S. Cl. ........................ 128/207.13; 128/205.25; 128/206.21; 128/206.26
(58) Field of Search .................. 128/205.25, 206.12, 128/206.18, 206.71, 206.21, 206.27, 206.28, 207.12, 207.13

(56) References Cited

U.S. PATENT DOCUMENTS

| | | |
|---|---|---|
| 2,011,733 A | 8/1935 | Shindel |
| 2,104,016 A | 1/1938 | Biggs |
| 2,254,854 A | 9/1941 | O'Connell |
| 2,317,608 A | 4/1943 | Heidbrink |
| 2,749,910 A | 6/1956 | Faulconer, Jr. |
| 2,931,356 A | 4/1960 | Schwarz |
| 2,939,458 A * | 6/1960 | Lundquist ............... 128/207.12 |
| 3,330,273 A * | 7/1967 | Bennett .................. 128/207.12 |
| 4,167,185 A * | 9/1979 | Lewis .................... 128/206.24 |
| 4,655,213 A | 4/1987 | Rapoport et al. |
| 4,677,977 A * | 7/1987 | Wilcox ................... 128/206.24 |
| 4,739,755 A | 4/1988 | White et al. |
| 4,907,584 A * | 3/1990 | McGinnis ............... 128/206.24 |
| 4,944,310 A | 7/1990 | Sullivan |
| 5,121,746 A * | 6/1992 | Sikora ................... 128/203.12 |
| D333,015 S | 2/1993 | Farmer et al. |
| 5,243,971 A | 9/1993 | Sullivan et al. |
| D349,586 S | 8/1994 | Handke |
| 5,353,789 A | 10/1994 | Schlobohm |
| 5,492,116 A | 2/1996 | Scarberry et al. |
| 5,540,223 A | 7/1996 | Starr et al. |
| 5,560,354 A | 10/1996 | Berthon-Jones et al. |
| 5,570,689 A | 11/1996 | Starr et al. |
| 5,647,357 A | 7/1997 | Barnett et al. |
| 5,660,171 A * | 8/1997 | Kimm et al. .......... 128/204.23 |
| 5,662,101 A * | 9/1997 | Ogden et al. .......... 128/205.25 |
| D389,238 S | 1/1998 | Kirk, III et al. |
| 5,724,965 A | 3/1998 | Handke et al. |
| 5,746,201 A * | 5/1998 | Kidd ..................... 128/206.24 |
| 5,778,872 A * | 7/1998 | Fukunaga et al. ...... 128/202.27 |
| 5,794,615 A * | 8/1998 | Estes .................... 128/204.23 |
| 5,884,624 A | 3/1999 | Barnett et al. |
| D412,745 S * | 8/1999 | Scheu ................... D24/110.4 |
| 5,970,975 A * | 10/1999 | Estes et al. ........... 128/204.23 |
| 6,006,748 A * | 12/1999 | Hollis ................... 128/205.24 |
| 6,192,886 B1 * | 2/2001 | Rudolph ................ 128/207.13 |

FOREIGN PATENT DOCUMENTS

WO  WO 98/04310  2/1998

* cited by examiner

Primary Examiner—John G. Weiss
Assistant Examiner—Joseph F. Weiss, Jr.
(74) Attorney, Agent, or Firm—Michael W. Haas

(57) ABSTRACT

A low contact nasal mask assembly that includes a seal member defined from a unitary piece of elastomeric material. The seal member defines a nose receiving cavity and has a first end portion and a second end portion generally opposite the first end portion. A first open is defined in the first end portion to allow at least a portion of a nose of a patient to enter the nose receiving cavity such that the nares of the patient communicate with the nose receiving cavity. The seal member also includes a neck portion defined in the second end portion and a second opening defined in the neck portion in communication with the nose receiving cavity. In addition, an outside diameter of the seal member and an inside diameter of the seal member increase generally linearly from the second end portion to the first end portion to minimize contact of the seal member with a patient and to minimize dead space. Furthermore, a collar coupled to the neck portion of the seal member provides a plurality of headgear attachment points spaced apart from the seal member. Also, a conduit coupling member is coupled to the collar and provides a mounting by which the nasal mask selectively couples to a breathing circuit.

28 Claims, 6 Drawing Sheets

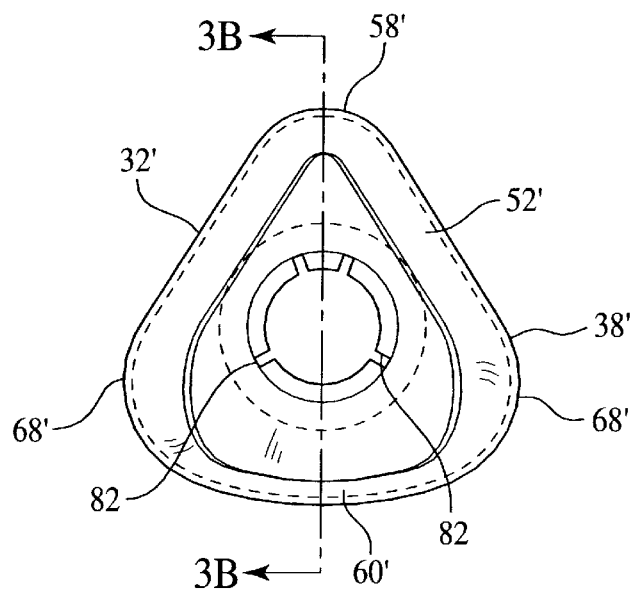
FIG. 3A
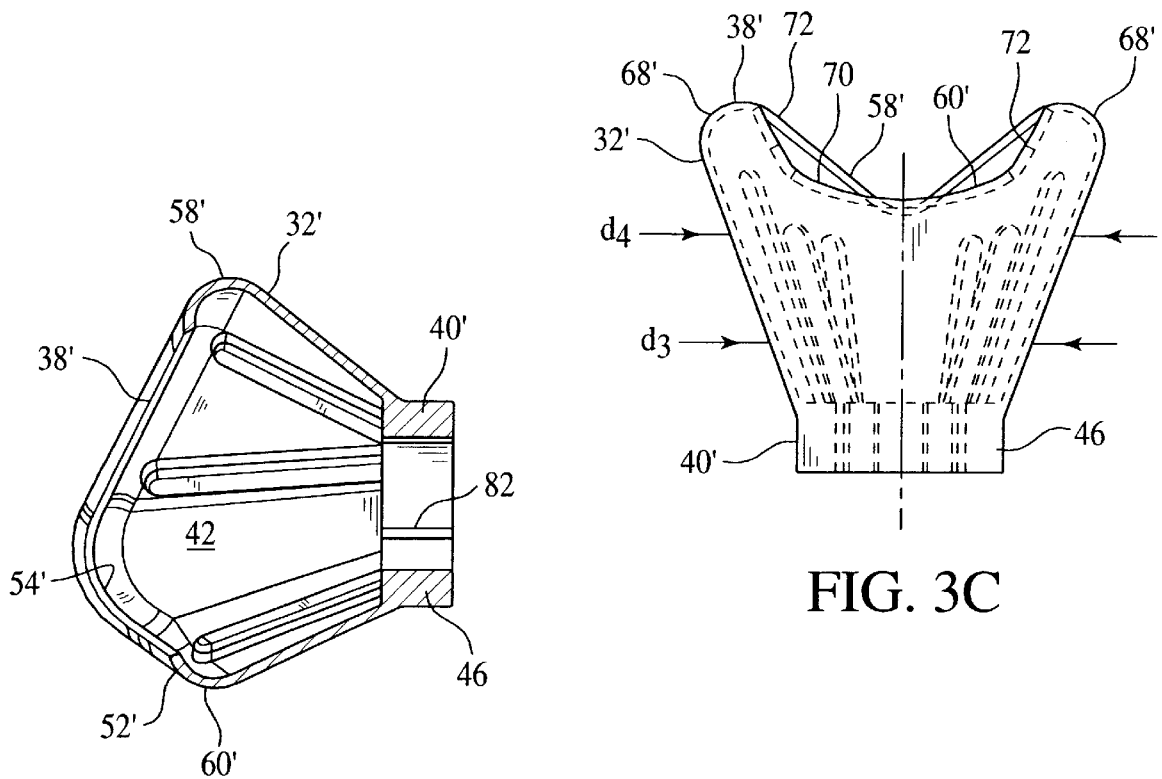
FIG. 3C
FIG. 3B

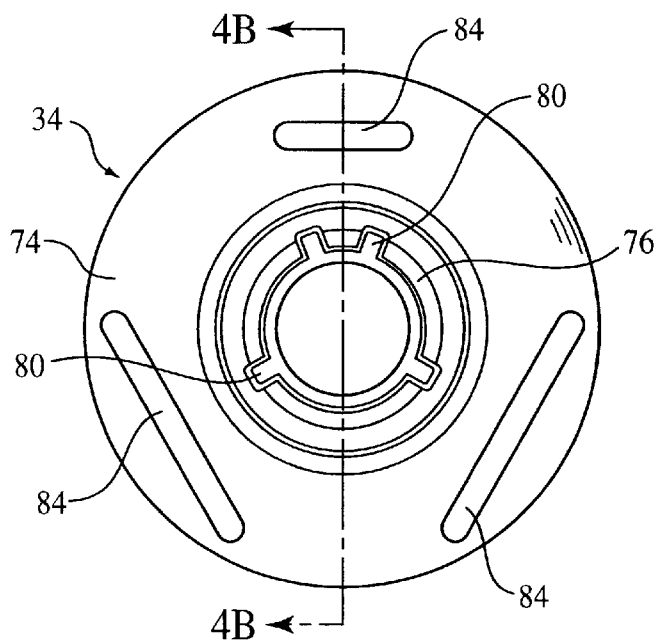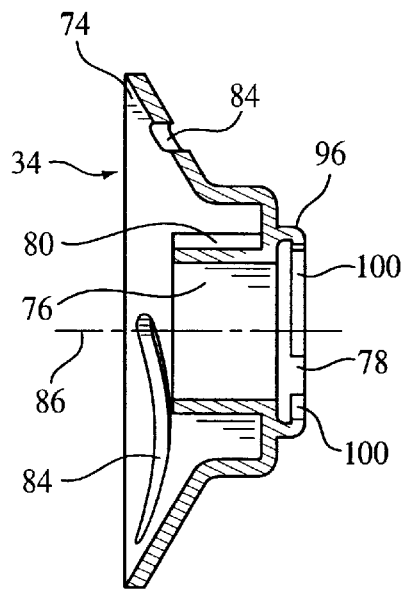
FIG. 4A
FIG. 4B
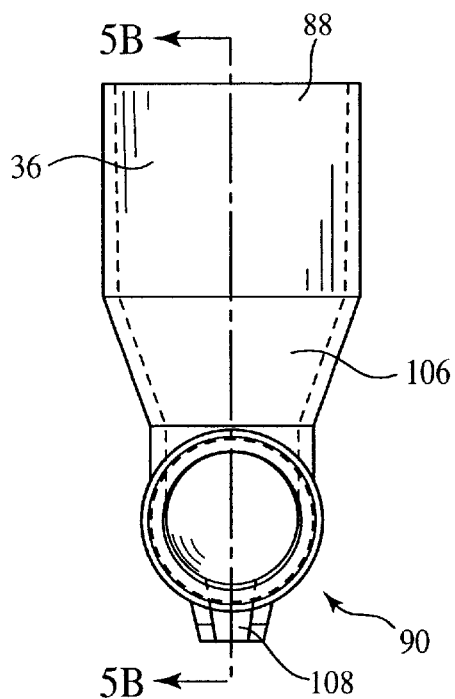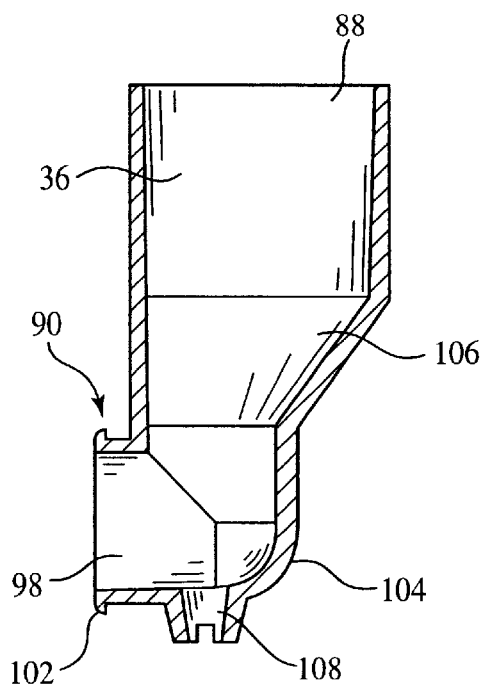
FIG. 5A
FIG. 5B

LOW CONTACT NASAL MASK AND SYSTEM USING SAME

BACKGROUND OF THE INVENTION

1. Field of the Invention

The present invention pertains to a low contact nasal mask and to a pressure support system using such a mask to interface with the airway of a patient, and, in particular, to a low contact nasal mask that includes a one-piece, lightweight seal member defining a nose receiving cavity, a collar coupled to the seal member, and a conduit coupling member, and to a system for supplying a flow of gas to a patient that incorporates such a low contact nasal mask.

2. Description of the Related Art

There are numerous situations where it is necessary or desirable to deliver a flow of breathing gas non-invasively to the airway of a patient, i.e., without intubating the patient or surgically inserting an tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure. Non-invasive ventilation and pressure support therapies involve the placement of a patient interface device, which is typically a nasal/oral mask, on the face of patient to interface the ventilator or pressure support device with the airway of the patient so that a flow of breathing gas can be delivered from the pressure/flow generating device to the airway of the patient.

Because such patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the user may avoid wearing the interface device, defeating the purpose of the prescribed pressure support therapy. Interrelated with the patient comfort concern is the need for the patient interface device to provide an effective seal with the patient's face to minimize leaks between the patient and the patient interface device throughout the therapy. Providing a good seal improves the operating efficiency of the pressure support or ventilatory therapy and also improves patient comfort by preventing or minimizing mask leaks, especially mask leaks that are directed toward the patient's eyes, which tend to dry the eyes causing discomfort.

SUMMARY OF THE INVENTION

Accordingly, it is an object of the present invention to provide a nasal mask assembly that addresses the above identified concerns and that overcomes shortcomings of conventional patient interface devices. This object is achieved according to one embodiment of the present invention by providing a nasal mask assembly that includes a seal member defined from a unitary piece of elastomeric material. The seal member includes a nose receiving cavity, a first end portion, a second end portion generally opposite the first end portion. A first opening is defined in the first end portion to receive at least a portion of a nose of a patient such that nares of the patient communicate with the receiving cavity. The seal member also includes a neck portion defined in the second end portion and a second opening defined in the neck portion to provide an inlet for breathing gas from an external source and an outlet for the patient's expelled gases. In addition, an outside diameter and an inside diameter of the seal member increase generally linearly from the second end portion to the first end portion to minimize contact of the seal member with a patient as well as dead space within the seal member. The nasal mask assembly also includes a collar coupled to the neck portion. The collar includes a plurality of headgear attachment points spaced apart from the seal member. In addition, the nasal mask assembly includes a conduit coupling member coupled to either the neck portion of the seal member and the collar for use in attaching the nasal mask assembly to a ventilator or pressure support device.

It is a further object of the present invention to provide a system for delivering a flow of gas to a patient that addresses the above identified concerns and that does not suffer from the shortcomings of conventional techniques. This object is achieved by providing a system for delivering a flow of gas to a patient that includes a gas flow generating device capable of producing a flow of gas and a conduit having a first end portion operatively coupled to the gas flow generating device and a second end portion. The conduit carries the flow of gas from the gas flow generating device. The system includes a nasal mask assembly operatively coupled to the second end portion of the conduit. The nasal mask assembly includes a seal member defined from a unitary piece of elastomeric material. The seal member includes a nose receiving cavity defined therein, a first end portion, and a second end portion generally opposite the first end portion. A first open is defined in the first end portion to allow at least a portion of the patient's nose to be inserted into the nose receiving cavity so that the nares of the patient communicate with the nose receiving cavity. The seal member also includes a neck portion defined in the second end portion, and a second opening defined in the neck portion. The second opening communicates with the nose receiving cavity to provide an inlet for breathing gas from the gas flow generating device and an outlet for the patient's expelled gases. In addition, an outside diameter of the seal member and an inside diameter of the seal member increase generally linearly from the second end portion to the end portion to minimize contact of the seal member with a patient and dead space.

The nasal mask assembly in the system for delivering a flow of gas to a patient further includes a collar coupled to the neck portion. The collar includes plurality of headgear attachment points spaced apart from the seal member. In addition, the nasal mask assembly a conduit coupling member having a first end portion coupled to the neck portion of the seal member or to the collar, and a second end portion coupled to the second end portion of the conduit.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 3A is a front view of an alternative configuration for the seal member for the nasal mask assembly of the present invention, 3B is a sectional view of the seal member taken along line 3B—3B in FIGS. 3A, and 3C is a bottom view of this seal member of this alternative embodiment;

FIG. 4A is a rear view of a collar in the low contact nasal mask assembly of FIGS. 1A–1C, and 4B is a sectional view of the collar taken along line 4B—4B of FIG. 4A;

FIG. 5A is a front view of a conduit coupling member in the low contact nasal mask assembly of FIGS. 1A–1C, and 5B is a sectional view of the conduit coupling member taken along line 4B—4B of FIG. 4A;

DETAILED DESCRIPTION OF THE PRESENTLY PREFERRED EMBODIMENTS OF THE INVENTION

Figure 1A:
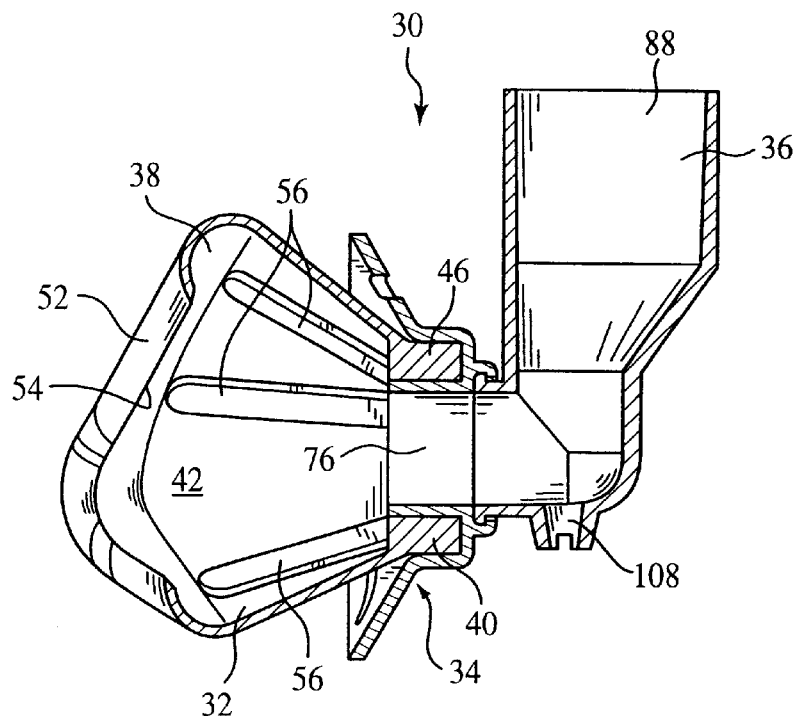
FIG. 1A is a sectional side view of a low contact nasal mask assembly according to the principles of the present invention taken along line 1A—1A in FIG. 1B.
Figure 1B:
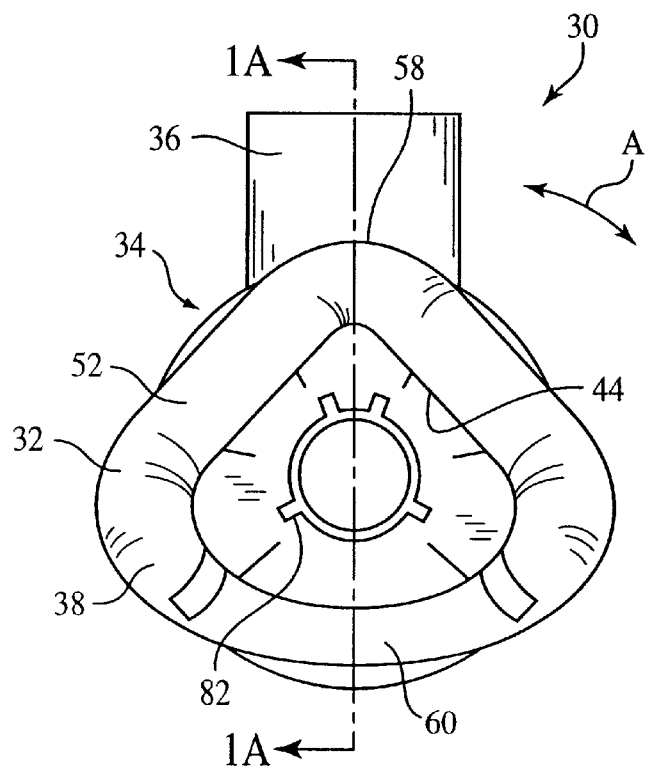
FIG. 1B is a front view of the nasal mask assembly.
Figure 1C:
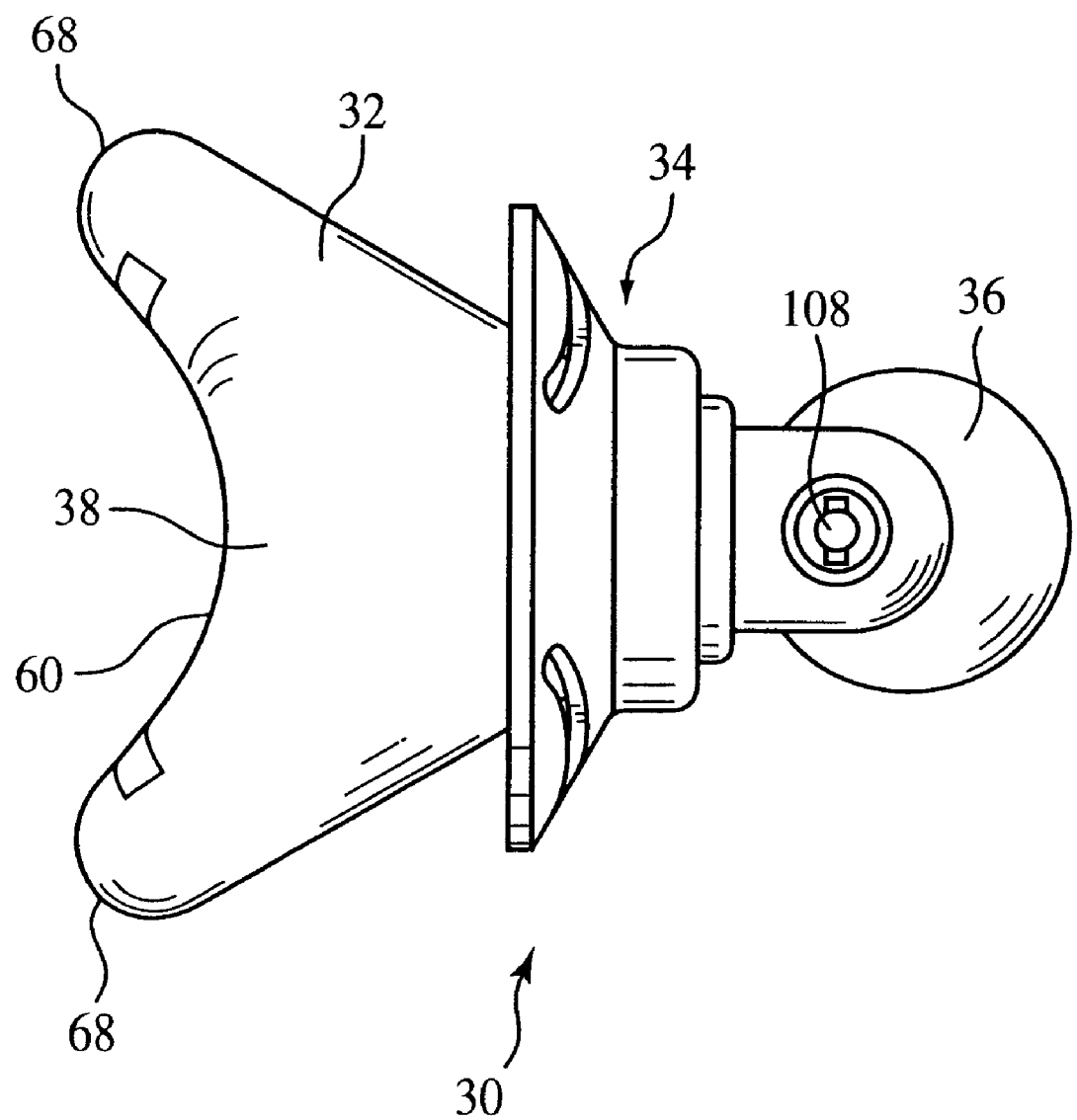
FIG. 1C is a bottom view the nasal mask assembly.
Figure 2A:
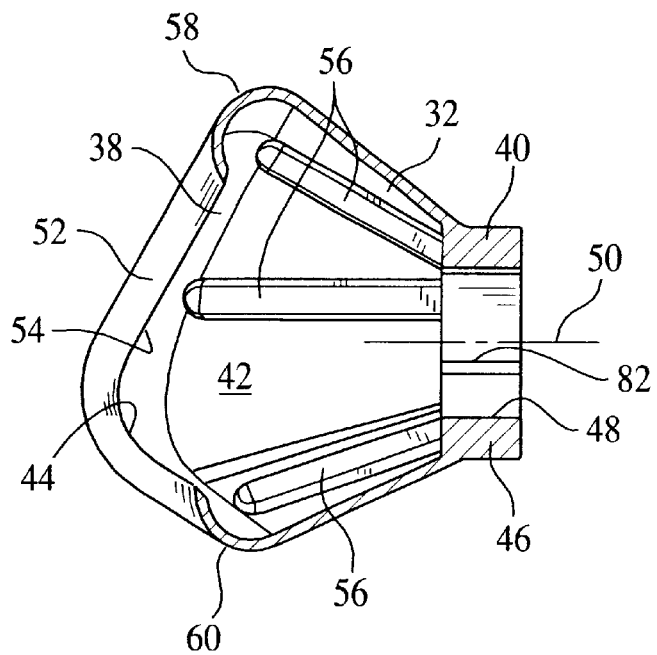
FIG. 2A is a sectional view and 2B is a bottom view of the seal member in the low contact nasal mask assembly of FIGS. 1A–1C.
Figure 2B:
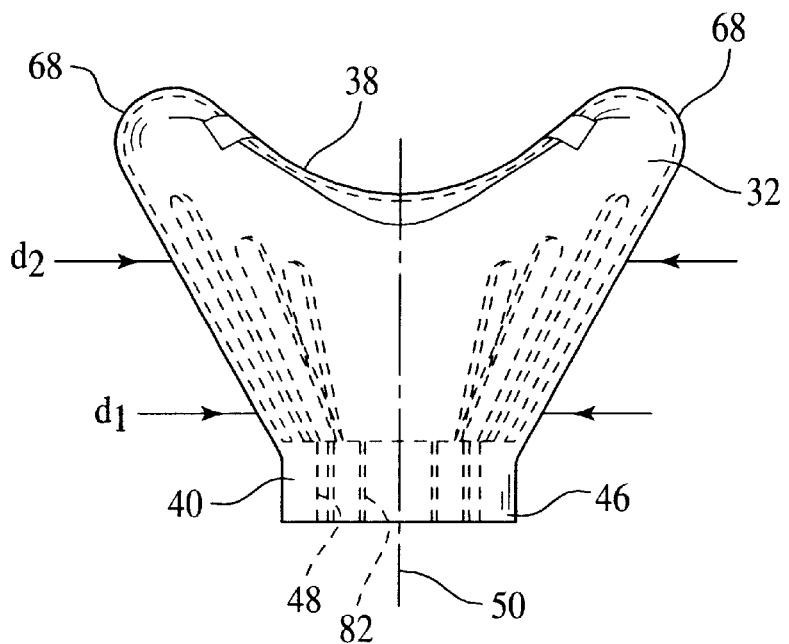

FIGS. 1A–1C illustrate an exemplary embodiment of a low contact nasal mask assembly 30 according to the principles of the present invention. As noted above, FIG. 1A is a sectional side view of nasal mask assembly 30 taken along line 1A—1A in FIG. 1B. FIG. 1B is a front view and FIG. 1C is a bottom view of the nasal mask assembly. Nasal mask assembly 30 functions as a patient interface device that communicates a flow of breathing gas between the patient's airway and a pressure generating device, such as a ventilator, CPAP device, or variable pressure device, e.g., a BiPAP® device manufactured and distributed by Respironics, Inc. of Pittsburgh, Pa., in which the pressure provided to the patient varies with the patient's respiratory cycle so that a higher pressure is delivered during inspiration than during expiration. Communicating a flow of breathing gas between the patient's airway and a pressure generating device includes delivering a flow of breathing gas to the patient from the pressure generating device and exhausting a flow of gas from the patient to ambient atmosphere.

Nasal mask assembly 30 includes a seal member 32, which contacts the patient's face, a collar 34, and a conduit coupling member 36. Seal member 32 is preferably fixed to a first side of collar 34 so that the seal member does not move relative to the collar. However, conduit coupling member 36 is preferably rotateably mounted on a second side of collar 34 opposite the first side so that conduit coupling member 36 freely rotates over a range of 360° about a central axis of collar 34, as generally indicated by arrow A in FIG. 1B. Details of exemplary embodiments of seal member 32, collar 34, conduit coupling member 36, and their interrelation with one another, including possible alternative configurations and preferred materials defining each of these items, are discussed below.

Figure 6:
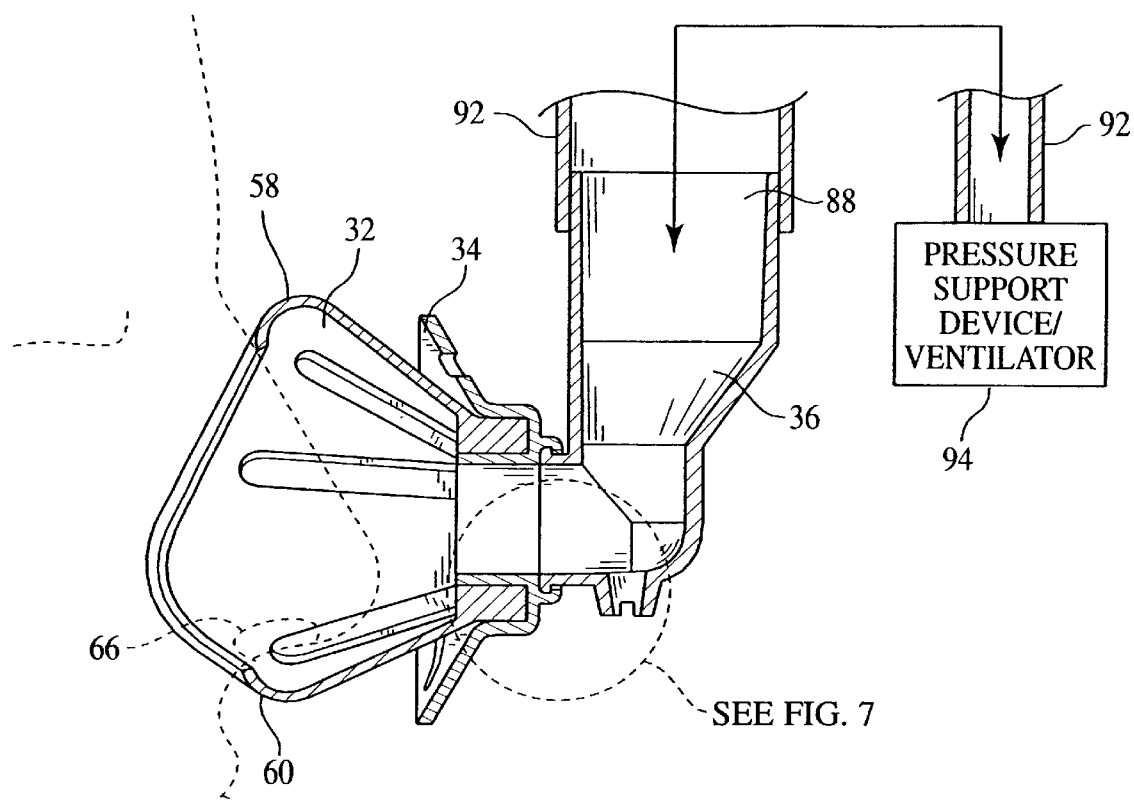
FIG. 6 is a side sectional view of a nasal mask assembly that schematically illustrated the nasal mask assembly in a system for delivering a gas to a patient.

As shown in FIGS. 1A–1C and 2A–2B, seal member 32 is preferably defined from a unitary piece of elastomeric material that is relatively flexible when a deformation force is applied thereto, yet returns to its original shape when the deformation force is removed. An example of a suitable material is silicone. Seal member 32 has a first end portion 38 and a second end portion 40 generally opposite first end portion 38 with a nose receiving cavity 42 defined therebetween. A first opening 44 is defined in first end portion 38 to allow passage of at least a portion of the patient's nose into nose receiving cavity 42. Seal member 38 is sized such that at least the distal end portion of the patient's nose, including the patient's nares, are disposed within nose receiving cavity 42 when the nasal mask assembly is properly positioned on the patient so that the patient's nares communicate with the nose receiving cavity. See FIG. 6.

Seal member 32 includes a neck portion 46 defined in second end portion 40 and a second opening 48 defined in neck portion 46. Second opening 48 communicates with nose receiving cavity 42 so that gas exhaled by the patient can be vented to atmosphere and gas can be delivered to the nares of the patient from an external source of breathing gas. In the illustrated embodiment, neck portion 46 is relatively thick as compared to a remainder of the seal member to provide a solid mounting base for the seal member. Also, in the illustrated embodiment, neck portion 46 is integral with seal member 32 so that neck portion 46 is formed from the same material as the remainder of the seal member. The present invention contemplates, however, that neck portion 46 can be made from a substance different from that of the remainder of the seal member and bonded thereto to define the illustrated seal member. Of course, the neck portion can also be made from the same substance as the rest of the seal member and bonded in place during the manufacturing process.

Seal member 32 is configured such that the outside diameter and the inside diameter increase in a generally linear fashion from second end portion 40 to first end portion 38. For example, outside diameter $d_1$ is less than outside diameter $d_2$, and the change in diameter from second end portion 40 to first end portion 38 increases in a generally linear fashion. In the illustrated embodiment, the walls of seal member 32 between first end portion 38 and second end portion 40 are of uniform thickness. Therefore, the inside diameter corresponding the location of outside diameter $d_1$ is likewise less than the inside diameter corresponding to the location of outside diameter $d_2$, and the increase in the inside diameter from second end portion 40 to first end portion 38 is also generally linear. In other words, the area of nose receiving cavity 42 lying in a plane that is normal to a central axis 50 and bisecting the seal member increases generally linearly from second end portion 40 to first end portion 38. Another way to describe the shape of seal member 32 is to consider a plane that bisects central axis 50. Such a plane corresponds to the section defined by line 1A—1A in FIG. 1B. Along a path from first end portion 38 to second end portion 40 in this plane, the distance between opposing side walls converge toward one another in a generally linear fashion.

This configuration for seal member 32 minimizes the size of the overall nasal mask assembly so that it can be made relatively lightweight. In addition, this configuration for the seal member minimizes the contact area of the nasal mask on the patient's face, which optimizes patient comfort, while providing complete encapsulation of at least the distal portion of the patient's nose, including the nares, in the nose receiving cavity for communicating gas with the patient's airway. In addition, this configuration for the nasal mask provides the above benefits while minimizing the dead space within the mask, thereby reducing the potential for rebreathing exhaled gas.

First end portion 38 of seal member 32 includes an in-turned lip 52 having a distal edge 54 that is generally turned inward into nose receiving cavity 42. An exposed surface of lip 52 contacts the patient's face when the nasal mask assembly is donned by the patient. The inward bend of lip 52 allows the lip to roll as the force by which the nasal mask assembly is pressed against the face increases, thereby reducing pressure points along the mask-patient interface. This force is commonly referred to as the "strapping force."

Because seal member 32 is formed from a relatively flexible material, a preferred embodiment for the seal member of the present invention includes a plurality of ribs 56 on the side walls of the seal member between first end portion 38 and second end portion 40. In the illustrated exemplary embodiment, ribs 56 extend from second end portion 40 toward first end portion 38 and provide structural support for the sides of the seal member so that the seal member does not collapse when a strapping force sufficient to minimizes leaks at the mask-patient interface is applied on second end portion 40. In a preferred embodiment of the present invention, ribs 56 are integrally formed with the seal member, and, therefore, are formed from the same material. In this embodiment, the ribs are approximately twice as thick as the remaining side wall portions of seal member 32. It can be appreciated, however, that ribs 56 can be made from substances that differ from that used to define seal member 32 and preferably fixedly secured thereto. Of course, the ribs can also be made from the same substance as seal member 32 and bonded on the inside surfaces during the manufacturing process. In addition, ribs 56 can have other thicknesses so long as they provide sufficient support for the side walls of the seal member.

Although the present invention illustrates three ribs on each side of seal member 32, it is to be understood that the position, as well as the shape for the ribs, can vary from that shown in the figures. The present invention also contemplates that the ribs can be eliminated in favor of increasing the thickness of the entire side wall, or a major portion of the side wall, of the seal member to provide the side wall support function. However, the weight of the seal member of this configuration, in which the thickness of the entire side wall is increased to prevent collapse of the side walls, is believed to be greater than the illustrated seal member having a plurality of ribs, and, therefore, is not preferred.

Seal member 32 is sized such when properly positioned on the patient, an uppermost portion 58 of first end portion 38 overlies a nose of a patient generally below a midpoint of the nose. In addition, a lowermost portion 60 of first end portion 38 overlies a portion of a patient 62 above upper lip 64 and below the patient's nares 66 when the nasal mask is properly positioned on the patient. See FIG. 6. This allows the distal end of the patient's nose to be encapsulated within the nose receiving cavity such that nares 66 communicate with the nose receiving cavity.

In addition, first end portion 38 of seal member 32 is contoured to correspond to the facial structure of a population of patients to improve comfort and reduce leaks. For example, first end portion 38 is formed into a generally triangular shape with distal side portions 68 extending relative to the remainder of first end portion 38 so as to overlie the flanks of the patient's nose. A nose receiving valley is defined at uppermost portion 58 of first end portion 38, and a lower valley is defined in lowermost portion 60 of first end portion 38. The shape of this lower valley is structured so as to generally match the shape of an area on the face above the upper lip and below the nose for a population of adult patients. For example, the lower valley in the lowermost portion of seal member 32 is generally rounded between side portions 68, which corresponds to the facial features of a relatively large population of adults.

It can be appreciated that the contour of the first end portion, size, and shape of the seal member can vary so that the seal member better corresponds to another population of patients, such as small adults and children. For example, a seal member 32' according to an alternative embodiment of the present invention is shown in FIGS. 3A–3C. Seal member 32' is specifically designed to correspond to the facial features of smaller patients, such as children, but is otherwise similar to seal member 32 of FIGS. 1A–2B. For example, seal member 32' includes a neck portion 46 that is substantially the same size and configuration as neck portion 46 in seal member 32 so that seal members 32 and 32' can be used in conjunction with a commonly sized collar 34 and conduit coupling member 36.

As with seal member 32, seal member 32' includes an outside diameter and an inside diameter that increases in a generally linear fashion from second end portion 40' to first end portion 38'. For example, outside diameter $d_3$ is less than outside diameter $d_4$, and the change in diameter from second end portion 40' to first end portion 38' increases in a generally linear fashion, as does the inside diameter. However, to accommodate smaller facial features, the change in diameter (outside and/or inside) from locations $d_3$ to $d_4$ is less than the change in diameter from locations $d_1$ to $d_2$ in FIGS. 2B, with the lateral distance from $d_3$ to $d_4$ being the same as the distance from $d_1$ to $d_2$. As a result, the distance between sides portions 68' at first end portion 38' of seal member 32' is less than that in seal member 32.

In addition, the contour on first end portion 38' in seal member 32' is somewhat different than the contour on first end portion 38 of seal member 32 to accommodate the smaller facial features of children and small adults. For example, a lowermost portion 60' of first end portion 38' in seal member 32' is shaped somewhat differently than lowermost portion 60 in seal member 32. Rather than being generally rounded between side portions 68, as with seal member 32, lowermost portion 60' in seal member 32' has a relatively rounded portion 70 and less rounded portions 72 on either side of rounded portion 70. Also, as can be appreciated from the figures, the steepness of the slopes of the nose receiving valley in uppermost portion 58' of seal member 32' is greater than that of the nose receiving valley in uppermost portion 58 of seal member 32.

Like seal member 32, seal member 32' includes an in-turned lip 52' at first end portion 38'. In the embodiment in FIGS. 3A–3C, however, the degree to which a distal edge 54' is turned toward nose receiving cavity 42' is less than that of lip 52 in FIGS. 1A–2B. Reducing the amount by which the distal edge is in-turned toward the nose receiving cavity reduces the contact area of the mask-patient interface. While the degree of roll in lip 52' is shown as being less than that of lip 52, the present invention contemplates that lip 52' can have the same or even a greater degree of roll than that of lip 52. Likewise, the degree of roll in lip 52 can also be increased or decreased depending on the desired seal and/or comfort to be provided to the patient. The greater the degree of roll, the more contact area there is between the mask assembly and the patient, which is beneficial, if, for example, the patient has deep contours, such as deep facial creases, over which the mask is to seal. The fact the a lesser degree of roll for the lip is shown in conjunction with seal member 32', which is specifically intended for use with children and/or small adults, is not germane. Different degrees of roll are not required between a large seal member intended for use with most adults, and a small seal member intended for use with most children. Rather, as noted above, the purpose of different degrees of roll is to alter the contact area of the seal member on the patient's face.

As discussed above with respect to FIGS. 1A–1C seal member 32, 32' attaches to collar 34, preferably such that the seal member does not move relative to the collar. In addition, the seal member preferably selectively attaches to the collar so that the seal member can be replaced with a new seal member. The details of collar 34 and the attachment of seal member 32, 32' thereto will now be discussed with continuing reference to FIGS. 1A–3C and with specific reference to FIGS. 4A–4B, which illustrate collar 34 in isolation.

Collar 34 includes a flange 74, a first mounting member 76 on one side of flange 74, and a coupling portion 78 on an opposite side of flange 74. Preferably collar 34 is defined by a unitary piece of material, such as a molded plastic, so that it is relatively rigid. First mounting member 76 selectively attaches the collar to a seal member, and coupling portion 78 attaches the collar to conduit coupling member 36.

In the illustrated embodiment, first mounting member 76 is sized and configured to insert within second opening 48 in neck portion 46 of seal member 32 with the friction between first mounting member 76 and neck portion 46 preventing the seal member from being readily pulled off of the collar. It is to be understood, however, that the present invention contemplates other configurations for coupling collar 34 and seal member 32. For example, neck portion 46 of seal member 32 and mounting member 76 of collar 34 can be configured such that the neck portion inserts within mounting member rather than mounting member 76 inserting within neck portion 46, as shown. In addition, a tongue and groove or other coupling structure can be provided on neck portion 46 of seal member 32 and mounting member 76 of collar 34 to maintain the neck portion in an engaged relation with the mounting member in addition to or in place of the friction engagement discussed above.

To prevent rotational movement of seal member 32 relative to collar 34, mounting member 76 includes a plurality of protrusions 80 and neck portion 46 includes an equal number of channels 82 adapted to receive protrusion 80 when seal member 32, 32' is properly positioned on collar 34. In addition to preventing rotation of seal member 32 relative to collar 34, protrusions 80 and channels 82 serve as guides for properly locating seal member 32, 32' on collar 34. Thus, it is preferable that protrusions 80 and channels 82 are configured and arranged such that they only align if seal member 32, 32' is properly positioned relative to collar 34.

While FIG. 4A illustrates four (4) protrusions 80 symmetrically disposed on mounting member 76 and FIGS. 1B and 3B illustrate four (4) channels 82 symmetrically disposed in the neck portions of seal members 32 and 32', respectively, it is to be understood that the present invention contemplates other configurations for protrusions 80 and channels 82, as well as increasing or decreasing the number of protrusions 80 and channels 82. For example, the present invention contemplates that a single protrusion and a single associated channel is sufficient to provide the rotation prevention and guide functions discussed above. In addition, the present invention contemplates reversing the placement of protrusions 80 and channels 82 so that the protrusion(s) is provided on the seal member and the reciprocal channel(s) is defined in the mounting member, or combinations thereof.

Flange 74 includes a plurality of cutouts 84 defined therein that function as headgear attachment points for securing a headgear (not shown) to collar 84. Cutouts 84 are defined at locations on flange 74 that are spaced apart from a central axis 86 of collar 34, and, hence, spaced apart from seal member 32 when the seal member is coupled to collar 34, to minimize and preferably prevent contact between the headgear straps attached at cutouts 84 and the seal member when the nasal mask assembly, including such headgear straps, is donned by a patient. That is, by locating the headgear attachment points away from central axis 84, which is aligned with central axis 50 (see FIG. 2B) of the seal member when the nasal mask is assembled, collar 34 prevents the headgear from interfering with the seal member, thereby ensuring that a proper and encumbered mask-patient seal is provided by the seal member. In addition, collar 34, by being sized and configured as shown, also provides a firm contact point for the relatively large headgear straps commonly used with patient interface device, while allowing the seal member to be made relatively small. Thus, specially sized straps are not required for use with the nasal mask assembly of the present invention.

While FIG. 4A illustrates collar 34 as having three cutouts as headgear attachment points, with the lower two cutouts being larger than the upper cutout, it is to be understood that the size and configuration for the cutouts is not limited to that shown in the figures. On the contrary, the present invention contemplates that cutouts 84 can have any configuration suitable to attach a headgear to the collar. In addition, cutouts 84 can be provided at locations other than those shown in the figures, but are preferably spaced apart from centerline 86 for the reasons presented above.

The present invention also contemplates that the headgear attachment need not be a cutout. Instead, the headgear attachment point can be defined by an attachment structure, such as a loop of rigid or flexible material fixed to flange 74. The present invention also contemplates that flange 74 can have a configuration other than the circular configuration shown in the figures, but is preferably configured to provide the headgear attachment points at locations spaced apart from centerline 86 for the reasons presented above. For example, flange 74 can have a star or triangle shape with each leg of the star or triangle serving as or providing a headgear attachment point.

Figure 7:
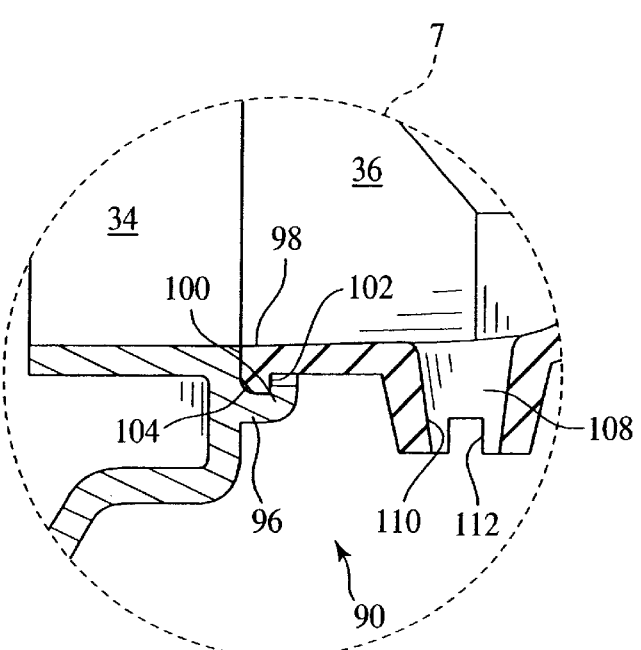
FIG. 7 is a detailed sectional view of a portion of the nasal mask assembly identified by numeral 7 in FIG. 6.

Coupling portion 78 in collar 34 preferably rotateably couples the collar to conduit coupling member 36. Details of conduit coupling member 36, as well as the structure for rotateably coupling the collar and the conduit coupling member according to an exemplary embodiment of the present invention are described below with reference to FIGS. 1A–7. FIGS. 5A–5B illustrate conduit coupling member 36 alone, and FIG. 7 is a detailed sectional view of the coupling portion of the nasal mask assembly identified by numeral 7 in FIG. 6.

Conduit coupling member 36 includes a conduit coupling portion 88 and a collar coupling portion 90. Conduit coupling portion 88 attaches conduit coupling member 36 to a patient circuit 92, such as a flexible conduit, which carries a flow of breathing gas generated by a flow generating device 94, such as a ventilator or pressure support device, to nasal mask assembly 30 and, hence, to nose receiving cavity 42. When the nasal mask assembly is donned by the patient, the flow of breathing gas delivered to the nose receiving cavity is delivered to the airway of the patient via the patient nares, which are located in the nose receiving cavity. In the illustrated embodiment, friction between conduit coupling portion 88 and patient circuit 92 maintain these items in an engaged relation. It is to be understood, however, that the present invention contemplates configuring conduit coupling portion 88 so that any conventional technique for coupling the tubular conduit coupling portion to the tubular patient circuit can be used.

Collar coupling portion 90 cooperates with coupling portion 78 in collar 34 to attach conduit coupling member 36 to collar 34. The present invention contemplates that the attachment between conduit coupling member 36 and collar 34 is either fixed or rotateable. However, the preferred configuration is to attach conduit coupling member 36 to collar 34 such that conduit coupling member 36 is rotateable over a 360° range relative to collar 34. See arrow A in FIG. 1B. Of course, the present invention also contemplates limiting the range of rotation so that conduit coupling member 36 is only allowed to rotate over a fixed range of rotational angles relative to collar 34. It should be understood that this fixed range of angles can be any range of angles within the 360° rotational circle.

In an exemplary embodiment of the present invention, rotateable engagement between conduit coupling member 36 and collar 34 is accomplished by providing a female mating member 96 in coupling portion 78 of collar 34 and a male mating member 98 in collar coupling portion 90 of conduit coupling member 36. In the illustrated embodiment, female mating member 96 is a circular ring protruding from a surface of flange 74 and male mating member 98 is a correspondingly shaped end portion of conduit coupling member 36. It is to be understood, however, that the present invention contemplates using other shapes, sizes and configurations for male and female mating members 98 and 96. For example, rather than protruding from collar 34, the female mating member can be defined within collar 34 by increasing the overall thickness of the collar at coupling portion 78. In addition, the male and female structures for mating members 96 and 98 can be reversed so that the male mating member is provided on the collar and the female mating member is provided on the conduit coupling member.

To maintain conduit coupling member 36 and collar 34 in an engaged relation while permitting rotational movement between the two, a first flange 100 is provided on an inside surface of female mating member 96 and a similar second flange 102 is provided on an outside surface of male mating member 98. Flanges 100 and 102 cooperate with one another, as best shown in FIG. 7, to maintain conduit coupling member 36 to collar 34 in an engaged relation while permitting rotational movement therebetween. Preferably, flange 102 on male mating member 98 includes a flat surface 104 to facilitate assembly of conduit coupling member 36 and collar 34.

In the illustrated exemplary embodiment, flange 100 is not continuous along the entire perimeter of the inside surface of female mating member 96. Instead, flange 100 includes a plurality of flange segments each spaced apart from an adjacent flange segment. It is to be understood, however, that the present invention contemplates defining flange 100 as a unitary flange extending around the entire inside perimeter of female mating member 96. Preferably, flange 102 extends around the entire outside perimeter of male mating member 98, as shown. It is to be understood, however, that the present invention contemplates defining flange 102 from a plurality of flange segments spaced apart along the outside perimeter of male mating member 98.

While the present invention illustrates coupling portion 78 of collar 34 and collar coupling portion 90 of conduit coupling member 36 as having flanges 100 and 102 for maintaining the collar and conduit coupling member in an engaged relation, it is to be understood that other structures for providing this rotateable coupling function are contemplated by the present invention. For example, a tongue and groove configuration can be provided on male and female mating member 98 and 96 for interlocking the structures.

As shown in the exemplary embodiment of the present invention, conduit coupling member 36 includes an elbow portion 104 adjacent collar coupling portion 90. It is to be understood, however, that elbow portion 104 can be eliminated in favor of a strait section. In addition, the degree of bend at the elbow portion need not be 90°, as shown, but can range between a variety of angles, such as 0°–95°. Conduit coupling member also includes a tapered portion 106 that serves to change the diameter from that of collar coupling portion 90 to that of conduit coupling portion 88, which corresponds to the diameter of a conventional patient circuit. It can be appreciated that the degree of taper in taper portion 106 can be varied over a relatively wide range depending on the change in diameter that is required to attach the nasal mask assembly to a patient circuit and the distance over which this transition in diameter is to be made. In addition, the taper portion can be eliminated if no taper is required, for example, if the size of second opening 48 in the seal member and the associated size of the collar and the collar coupling portion generally match the diameter of the patient circuits to which the nasal mask assembly is to attach.

Conduit coupling member 36 also includes an exhaust port 108 that communicates an interior of conduit coupling member 36 with ambient atmosphere. Exhaust port 108 allows the patient's exhaled gases to escape to atmosphere. In the illustrated embodiment, exhaust port 108 has an inside surface 110 whose diameter constantly tapers, i.e., decreases, in a direction from the interior of the conduit coupling member to an exterior thereof. The taper provided by inside surface 110 is believed to reduce noise associated with the exhausting of gas through the exhaust port. In addition, a plurality of cutouts 112 are defined in a distal end of exhaust port 108 so prevent or minimize blockage of the port.

In a preferred embodiment, exhaust port 108 is located relatively close to the nose receiving cavity in the seal member to minimize dead space. It is to be understood, however, that the present invention contemplates providing the exhaust port at other locations, including providing more than one exhaust port in the conduit coupling member. Furthermore, while exhaust port 108 is shown protruding from conduit coupling member 36, it is to be understood that other configurations for the exhaust port are possible. For example, the exhaust port can be flush with the walls of the conduit coupling member, so that the exhaust port is merely a hole defined in the wall of the conduit coupling member.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface device comprising:
    a collar defined from a relatively rigid material, the collar comprising:
        a flange having a first side and a second side opposite the first side, wherein an aperture is defined in a central portion of the flange to allow a gas to pass between the first side and the second side through the collar,
        a mounting member disposed on a first side of the flange,
        a conduit coupling portion disposed on a second side of the flange, and
        a plurality of headgear attachment points disposed on the flange; and a seal member defined from a pliable material and having a nose receiving cavity defined therein, the seal member comprising:
- a neck portion that is sized and configured so as to selectively engage the mounting member of the collar and to remain engaged therewith due to friction between the neck portion and the mounting member, wherein the neck portion includes a first opening defined therein that is sized and configured so as to communicate the nose receiving cavity with the aperture defined in the flange responsive to the seal member engaging the collar, thereby defining a gas flow path between the second side of the flange and the nose receiving cavity,
- a side wall extending from the neck portion and terminating generally at a first end portion that is adapted to contact a patient responsive to the patient interface device being donned by a patient, and wherein the first end portion includes a second opening defined therein that is sized and configured to receive at least a portion of a nose of such a patient so that nares of such a patient communicate with the nose receiving cavity.

2. A patient interface device according to claim 1, further comprising a conduit coupling member operatively coupled to the collar via the conduit coupling portion.

3. A patient interface device according to claim 2, wherein the conduit coupling member is rotateably coupled to the collar via the conduit coupling portion.

4. A patient interface device according to claim 2, wherein the conduit coupling member includes an elbow having an exhaust port defined therein.

5. A patient interface device according to claim 1, wherein the mounting member protrudes from the flange, and wherein the neck portion and the mounting member are sized and configured such that the mounting member is disposed within the first opening in the neck member responsive to the seal member engaging the collar.

6. A patient interface device according to claim 5, wherein the mounting member, the neck portion, and the flange are configured and arranged such that a distal end of the neck portion contacts the flange responsive to the seal member fully engaging the collar, thereby limiting a distance into which the mounting member inserts into the first opening of the neck member.

7. A patient interface device according to claim 1, wherein the neck portion and flange are sized and configured such that a surface of the neck portion engages a surface of the flange and remains engaged therewith due to friction between the neck portion and the surface of the flange responsive to the seal member engaging the collar.

8. A patient interface device according to claim 1, wherein the neck portion and the mounting member include a tongue and groove assembly.

9. A patient interface device according to claim 1, wherein the first end portion of the seal member includes an in-turned lip having a distal edge that is generally turned toward the nose receiving cavity.

10. A patient interface device according to claim 1, wherein the seal member includes a plurality of ribs disposed on the side wall to provide structural support for the side wall of the seal member.

11. A patient interface device according to claim 1, wherein the collar is arranged and configured such that the plurality of headgear attachment points are maintained in a spaced apart relation from the seal member to minimize contact between headgear straps that are attachable to the collar at the plurality of headgear attachment points and the seal member responsive to the patient interface device, including such headgear straps, being donned by a patient.

12. A patient interface device according to claim 1, wherein the neck portion is substantially thicker than a remainder of the seal member to provide a relatively stable mounting base for attaching the seal member to the collar.

13. A patient interface device according to claim 1, wherein the first end portion is contoured to correspond to a facial structure of a human.

14. A system for delivering a breathing gas to a patient, comprising:
- a gas flow generating device that produces a flow of gas;
- a conduit having a first end portion operatively coupled to the gas flow generating device and a second end portion, wherein the conduit carries the flow of gas from the gas flow generating device during operation of the system; and
- a patient interface device operatively coupled to the second end portion of the conduit, the patient interface device comprising:
  - a collar defined from a relatively rigid material, the collar comprising:
    - a flange having a first side and a second side opposite the first side, wherein an aperture is defined in a central portion of the flange to allow a gas to pass between the first side and the second side through the collar,
    - a mounting member disposed on a first side of the flange,
    - a conduit coupling portion disposed on a second side of the flange and operatively coupling the flange to the second end portion of the conduit, and
    - a plurality of headgear attachment points disposed on the flange; and
  - a seal member defined from a pliable material and having a nose receiving cavity defined therein, the seal member comprising:
    - a neck portion that is sized and configured so as to selectively engage the mounting member of the collar and to remain engaged therewith due to friction between the neck portion and the mounting member, wherein the neck portion includes a first opening defined therein that is sized and configured so as to communicate the nose receiving cavity with the aperture defined in the flange responsive to the seal member engaging the collar, thereby defining a gas flow path between the second side of the flange and the nose receiving cavity,
    - a side wall extending from the neck portion and terminating generally at a first end portion that is adapted to contact a patient responsive to the patient interface device being donned by a patient, and wherein the first end portion includes a second opening defined therein that is sized and configured to receive at least a portion of a nose of such a patient so that nares of such a patient communicate with the nose receiving cavity.

15. A system according to claim 14, further comprising a conduit coupling member interposed between the collar and the second end of the conduit, wherein the conduit coupling member has a first end operatively coupled to the collar via the conduit coupling portion and a second end operatively coupled to the second end of the conduit.

16. A system according to claim 15, wherein the conduit coupling member is rotateably coupled to the collar via the conduit coupling portion.

17. A system according to claim 15, wherein the conduit coupling member includes an elbow having an exhaust port defined therein.

18. A system according to claim 14, wherein the mounting member protrudes from the flange, and wherein the neck portion and the mounting member are sized and configured such that the mounting member is disposed within the first opening in the neck member responsive to the seal member engaging the collar.

19. A system according to claim 18, wherein the mounting member, the neck portion and the flange are configured and arranged such that a distal end of the neck portion contacts the flange responsive to the seal member fully engaging the collar, thereby limiting a distance into which the mounting member inserts into the first opening of the neck member.

20. A system according to claim 14, wherein the neck portion and flange are sized and configured such that a surface of the neck portion engages a surface of the flange and remains engaged therewith due to friction between the neck portion and the surface of the flange responsive to the seal member engaging the collar.

21. A system according to clam 14, wherein the neck portion and the mounting member include a tongue and groove assembly.

22. A system according to claim 14, wherein the first end portion of the seal member includes an in-turned lip having a distal edge that is generally turned toward the nose receiving cavity.

23. A system according to claim 14, wherein the seal member includes a plurality of ribs disposed on the side wall to provide structural support for the side wall of the seal member.

24. A system according to claim 14, wherein the collar is arranged and configured such that the plurality of headgear attachment points are maintained in a spaced apart relation from the seal member to minimize contact between headgear straps that are attachable to the collar at the plurality of headgear attachment points and the seal member responsive to the patient interface device, including such headgear straps, being donned by a patient.

25. A system according to claim 14, wherein the neck portion is substantially thicker than a remainder of the seal member to provide a relatively stable mounting base for attaching the seal member to the collar.

26. A system according to claim 14, wherein the first end portion is contoured to correspond to a facial structure of a human.

27. A patient interface device comprising:
a collar defined from a relatively rigid material, the collar comprising:
a flange having a first side and a second side opposite the first side, wherein an aperture is defined in a central portion of the flange to allow a gas to pass between the first side and the second side through the collar,
mounting means, disposed on a first side of the flange, for attaching a seal member to the collar,
a conduit coupling portion disposed on a second side of the flange, and
a plurality of headgear attachment points disposed on the flange; and
a seal member defined from a pliable material with a nose receiving cavity defined therein, the seal member comprising:
a neck portion that is sized and configured so as to selectively engage the mounting means and to remain engaged therewith due to friction between the neck portion and the mounting means, wherein the neck portion includes a first opening defined therein that is sized and configured so as to communicate the nose receiving cavity with the aperture defined in the flange responsive to the seal member engaging the collar, thereby defining a gas flow path from the second side of the flange to the nose receiving cavity,
a side wall extending from the neck portion and terminating generally at a first end portion that is adapted to contact a patient responsive to the patient interface device being donned by a patient, and wherein the first end portion includes a second opening defined therein that is sized and configured to receive at least a portion of a nose of such a patient so that nares of such a patient communicate with the nose receiving cavity.

28. A patient interface device according to claim 27, wherein the mounting means is defined by a portion of the flange engaging the neck portion of the seal responsive to the seal member engaging the collar.

* * * * *